US012778995B2

(12) United States Patent
Lin et al.

(10) Patent No.: US 12,778,995 B2
(45) Date of Patent: *Nov. 3, 2026

(54) METHOD OF USING A COMBINATION OF POSTBIOTICS AND PROBIOTICS FOR PREVENTION OF SEVERE ACUTE RESPIRATORY SYNDROME CORONAVIRUS 2 INFECTION- ASSOCIATED DISORDERS

(71) Applicant: CHAMBIO CO., LTD., Taichung City (TW)

(72) Inventors: Meei-Yn Lin, Taichung City (TW); Hung-Pin Chiu, Taichung City (TW); Yi-Heng Chiu, Taichung City (TW)

(73) Assignee: CHAMBIO CO., LTD., Taichung City (TW)

( * ) Notice: Subject to any disclaimer, the term of this patent is extended or adjusted under 35 U.S.C. 154(b) by 360 days.

This patent is subject to a terminal disclaimer.

(21) Appl. No.: 18/499,450

(22) Filed: Nov. 1, 2023

(65) Prior Publication Data

US 2024/0398878 A1 Dec. 5, 2024

(30) Foreign Application Priority Data

May 31, 2023 (TW) ................................ 112120383

(51) Int. Cl.

| | |
|---|---|
| ***A61P 11/00*** | (2006.01) |
| ***A61K 35/742*** | (2015.01) |
| ***A61K 35/747*** | (2015.01) |
| ***A61P 29/00*** | (2006.01) |
| ***A61P 31/14*** | (2006.01) |

(52) U.S. Cl.

CPC .......... *A61K 35/747* (2013.01); *A61K 35/742* (2013.01); *A61P 11/00* (2018.01); *A61P 29/00* (2018.01); *A61P 31/14* (2018.01)

(58) Field of Classification Search

CPC ................ A61K 35/747; A61K 35/742; A61K 2035/115; A61K 9/0053; A61P 11/00; A61P 29/00; A61P 31/14; A61P 37/02; A23L 33/135; A23V 2002/00

See application file for complete search history.

(56) References Cited

U.S. PATENT DOCUMENTS 11,446,338 B2 * 9/2022 Farber .................. A61K 35/742 424/50

FOREIGN PATENT DOCUMENTS

CN 112843096 A * 5/2021 ........... A61K 35/742

OTHER PUBLICATIONS

Irfan A. Rather, Manipulated bio antimicrobial peptides from probiotic bacteria as proposed drugs for COVID-19 disease, Vaccines, 9, 1067. (Year: 2021).*

Negar Balmeh, Potential Adjuvant Therapeutic Effect of Lactobacillus plantarum Probio-88, Informatics in Medicine Unlocked 23 100515Postbiotics against SARS-COV-2 (Year: 2021).*

* cited by examiner

*Primary Examiner* — Melenie L Gordon
*Assistant Examiner* — Tiffany M Gough
(74) *Attorney, Agent, or Firm* — MH2 Technology Law Group, LLP

(57) ABSTRACT

A method for preventing a severe acute respiratory syndrome coronavirus 2 (SARS-CoV-2) infection-associated disorder includes use of a composition containing live *Bacillus coagulans* CB85 which is deposited under the Budapest Treaty at the Deutsche Sammlung von Mikroorganismen und Zellkulturen (DSMZ) GmbH under an accession number DSM 33893, and heat-killed *Lactobacillus plantarum* CB102 which is deposited under the Budapest Treaty at the DSMZ GmbH under an accession number DSM 33894.

4 Claims, 13 Drawing Sheets

METHOD OF USING A COMBINATION OF POSTBIOTICS AND PROBIOTICS FOR PREVENTION OF SEVERE ACUTE RESPIRATORY SYNDROME CORONAVIRUS 2 INFECTION- ASSOCIATED DISORDERS

CROSS-REFERENCE TO RELATED APPLICATION

This application claims priority to Taiwanese Invention Patent Application No. 112120383, filed on May 31, 2023, and incorporated by reference herein in its entirety.

FIELD

The present disclosure relates to a method for preventing a severe acute respiratory syndrome coronavirus 2 (SARS-CoV-2) infection-associated disorder using a composition including live *Bacillus coagulans* CB85 and heat-killed *Lactobacillus plantarum* CB102.

BACKGROUND

Coronavirus disease 2019 (COVID-19) is an acute respiratory disease caused by severe acute respiratory syndrome coronavirus 2 (SARS-CoV-2), which is an enveloped, positive-sense, single-stranded RNA betacoronavirus. Infection with the SARS-CoV-2 may lead to uncontrolled inflammatory response, release of large amounts of pro-inflammatory cytokines, and result in lymphopenia, lymphocyte dysfunction, and granulocyte and monocyte abnormalities. If the SARS-CoV-2 stays in the body of a host for a long period of time, immune escape may occur to evade the immune system of the host, or an exaggerated and prolonged immune response (i.e., cytokine storm) may ensue, causing lung inflammation which includes pneumonia and pulmonary infiltrate, and lung injury which includes acute respiratory distress syndrome (ARDS) and chronic obstruction pulmonary disease (COPD).

Moreover, some patients with COVID-19 may even develop multisystem inflammatory syndrome (MIS), which causes severe inflammation of multiple organs, and in severe cases, cardiovascular function may be affected, leading to acute heart failure (AHF), shock, or death.

Some drugs have been found to be helpful in the treatment of SARS-CoV-2 infection, but showed adverse effects as reported in experimental studies and clinical trials. For instance, Paxlovid, an oral antiviral pill, is considered a first option for treating mild to moderate SARS-CoV-2 infection in patients at high risk of developing severe illnesses. However, Paxlovid exhibited side effects that include taste change, diarrhea, high blood pressure, headache, liver damage, and nausea. In addition, Remdesivir, administered via intravenous injection, is used to treat mild to moderate SARS-CoV-2 infection in patients at high risk of developing severe illnesses. The most common side effects reported in studies using Remdesivir for treating SARS-CoV-2 infection include respiratory failure, organ dysfunction, gastrointestinal distress, increased levels of transaminases in the blood, and injection site reaction. Therefore, boosting of immune system is crucial to prevent SARS-CoV-2 infection.

In view of the foregoing, there is still a need to develop an effective way for preventing a SARS-CoV-2 infection-associated disorder without adversely affecting normal immune function.

SUMMARY

Therefore, an object of the present disclosure is to provide a method for preventing a severe acute respiratory syndrome coronavirus 2 (SARS-CoV-2) infection-associated disorder, which can alleviate at least one of the drawbacks of the prior art, and which includes administering to a subject in need thereof a composition including live *Bacillus coagulans* CB85 and heat-killed *Lactobacillus plantarum* CB102.

The live *Bacillus coagulans* CB85 is deposited under the Budapest Treaty at the Deutsche Sammlung von Mikroorganismen und Zellkulturen (DSMZ) GmbH under an accession number DSM 33893, and the heat-killed *Lactobacillus plantarum* CB102 is deposited under the Budapest Treaty at the DSMZ GmbH under an accession number DSM 33894.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
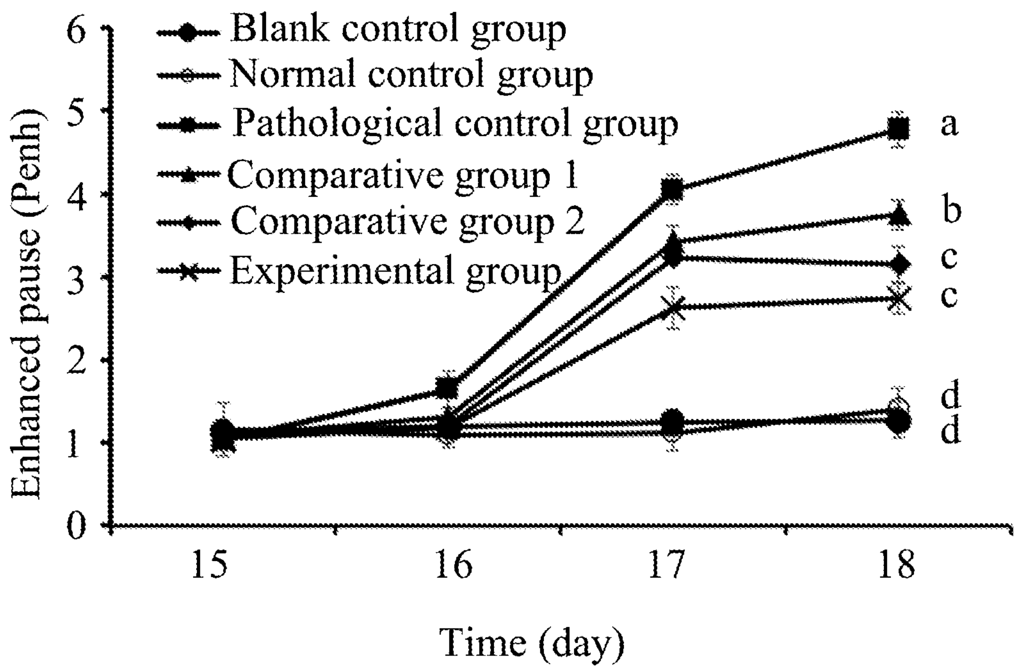
FIG. 1 shows the change in enhanced pause (Penh) determined over time in each group of mice of Example 1, infra, in which: the English letters indicate the results of statistical analyses; if any two groups have the same English letter, there is no significant difference between the two groups; and if any two groups do not have the same English letter, there is a significant difference between the two groups ($p<0.05$).

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a method for preventing a severe acute respiratory syndrome coronavirus 2 (SARS-CoV-2) infection-associated disorder, which includes administering to a subject in need thereof a composition containing live *Bacillus coagulans* CB85 and heat-killed *Lactobacillus plantarum* CB102.

The live *Bacillus coagulans* CB85 is deposited under the Budapest Treaty at the Deutsche Sammlung von Mikroorganismen und Zellkulturen (DSMZ) GmbH under an accession number DSM 33893, and the heat-killed *Lactobacillus plantarum* CB102 is deposited under the Budapest Treaty at the DSMZ GmbH under an accession number DSM 33894.

As used herein, the term "preventing" or "prevention" means eliminating or reducing the incidence of a SARS-CoV-2 infection-associated disorder, or slowing, delaying, controlling, or decreasing the likelihood or probability of a SARS-CoV-2 infection-associated disorder.

As used herein, the term "administration" or "administering" means introducing, providing or delivering a predetermined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

According to the present disclosure, the live *Bacillus coagulans* CB85 serves as a probiotic strain, and the heat-killed *Lactobacillus plantarum* CB102 serves as a postbiotic component.

According to the present disclosure, the SARS-CoV-2 infection-associated disorder may be selected from the group consisting of lung inflammation (such as pneumonia and pulmonary infiltrate), lung injury (such as acute respiratory distress syndrome (ARDS) and chronic obstruction pulmonary disease (COPD)), lymphopenia, granulocyte abnormalities, immune escape (also known as immune evasion), cytokine storm, multisystem inflammatory syndrome (MIS) (such as multisystem inflammatory syndrome in children (MIS-C) and multisystem inflammatory syndrome in adult (MIS-A)), and combinations thereof.

In certain embodiments, a number ratio of the live *Bacillus coagulans* CB85 and the heat-killed *Lactobacillus plantarum* CB102 ranges from 1:0.1 to 1:10. In an exemplary embodiment, the number ratio of the live *Bacillus coagulans* CB85 and the heat-killed *Lactobacillus plantarum* CB102 is 1:1.47.

As used herein, the term "heat-killed" can be used interchangeably with other terms such as "heat-inactivated" and "tyndallization", and refers to subjecting probiotics to a heat treatment for a predetermined time period so as to kill them.

The heat-killed *Lactobacillus plantarum* CB102 may be prepared using techniques well-known to those skilled in the art. In this regard, those skilled in the art may refer to journal articles, e.g., S. Murosaki, et al. (1998) *J. Allergy Clin. Immunol.* 102(1): 57-64, and S. Segawa, et al. (2008) *Int. J. Food Microbiol.* 128(2): 371-377.

In certain embodiments, the heat-killed *Lactobacillus plantarum* CB102 may be prepared by subjecting *Lactobacillus plantarum* CB102 to a heat treatment at a temperature ranging from 60° C. to 140° C. for a time period ranging from 1 second to 30 minutes. In an exemplary embodiment, the heat treatment is performed at a temperature of 73±2° C. for a time period of 15 seconds.

According to the present disclosure, each lactic acid bacterial strain may be prepared by culturing the abovementioned lactic acid bacterial strain in a liquid or solid medium suitable for growth and/or proliferation thereof. In an exemplary embodiment, the abovementioned lactic acid bacterial strain is cultivated in a liquid medium suitable for growth thereof, so as to form a liquid culture.

According to the present disclosure, the liquid culture of each lactic acid bacterial strain may be further subjected to a drying treatment using techniques well-known to those skilled in the art. Examples of the drying treatment may include, but are not limited to, a spray-drying treatment, a lyophilization treatment, a vacuum evaporation treatment, and combinations thereof. In an exemplary embodiment, the liquid culture of each lactic acid bacterial strain is subjected to a spray-drying treatment.

According to the present disclosure, the liquid culture of each lactic acid bacterial strain, prior to being subjected to the drying treatment, is first subjected to a separation treatment so as to remove a liquid medium used.

In certain embodiments, the separation treatment may be performed using techniques well-known to those skilled in the art. Examples of the separation treatment may include, but are not limited to, a centrifugation treatment, a filtration treatment, and a combination thereof. In an exemplary embodiment, the separation treatment is a centrifugation treatment.

According to the present disclosure, the composition may be formulated as a food product using a standard technique well known to one of ordinary skill in the art. For example, the composition may be directly added to an edible material or may be used to prepare an intermediate composition (e.g., a premix) suitable to be subsequently added to the edible material.

As used herein, the term "food product" refers to any article or substance that can be ingested by a subject into the body thereof. Examples of the food product may include, but are not limited to, milk powders, fermented milk, yogurt, butter, beverages (e.g., tea, coffee, etc.), functional beverages, a flour product, baked foods, confectionery, candies, fermented foods, animal feeds, health foods, and dietary supplements.

According to the present disclosure, the food product may further include an additional food additive selected from the group consisting of starch, dextrin, lactose, maize flour, rice flour, tricalcium phosphate, silicon dioxide, magnesium stearate, calcium carbonate, glucose, sucrose, fructose, sugar alcohol, oligosaccharides, sugar substitutes, fruit juice powders, yeast powders, nonfat dry milk, casein, whey proteins, amino acids, citric acid, citrate, lactic acid, lactate, nucleotides, and combinations thereof.

According to the present disclosure, the composition may be prepared in the form of a pharmaceutical composition. The pharmaceutical composition may be formulated into a suitable dosage form for oral administration using technology well known to those skilled in the art.

According to the present disclosure, the dosage form suitable for oral administration includes, but is not limited to, sterile powders, tablets, troches, lozenges, pellets, capsules, dispersible powders or granules, solutions, suspensions, emulsions, syrup, elixir, slurry, and the like. In certain embodiments, the pharmaceutical composition is formulated into a capsule dosage form.

According to the present disclosure, the pharmaceutical composition may further include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the aforesaid agents are within the expertise and routine skills of those skilled in the art.

According to the present disclosure, the dose and frequency of administration of the composition may vary depending on the following factors: the severity of the illness or disorder to be treated, routes of administration, and age, physical condition and response of the subject to be treated. In general, the composition may be administered in a single dose or in several doses.

The disclosure will be further described by way of the following examples. However, it should be understood that the following examples are solely intended for the purpose of illustration and should not be construed as limiting the disclosure in practice.

EXAMPLES

General Experimental Materials

1. Lactic Acid Bacterial (LAB) Strains

*Bacillus coagulans* CB85 and *Lactobacillus plantarum* CB102, which are known and readily available to the public, were obtained from the Microbiology Research Laboratory of the Department of Food Science and Biotechnology, National Chung-Hsing University, Taichung, Taiwan, and have been deposited at the Bioresource Collection and Research Center (BCRC) of the Food Industry Research and Development Institute (FIRDI) (No. 331, Shih-Pin Rd., Hsinchu City 300, Taiwan). In addition, these LAB strains have also been deposited under the terms of the Budapest Treaty on the International Recognition of the Deposit of Microorganisms for the Purpose of Patent Procedure at the International Depositary Authority, i.e., the Deutsche Sammlung von Mikroorganismen und Zellkulturen (DSMZ) GmbH (Inhoffenstraße 7B, 38124 Braunschweig, Germany) in accordance with the Budapest Treaty.

The relevant information regarding each of the LAB strains (including accession number and date of deposit) is listed in Table 1 below.

TABLE 1

| LAB strains | Accession number | Date of deposit |
|---|---|---|
| *Bacillus coagulans* CB85 | BCRC 911010<br>DSM 33893 | Jul. 23, 2020<br>Jun. 9, 2021 |
| *Lactobacillus plantarum* CB102 | BCRC 910893<br>DSM 33894 | May 8, 2019<br>Jun. 9, 2021 |

2. Preparation of Bacteria Powder of Live *Bacillus coagulans* CB85

The *Bacillus coagulans* CB85 as described in section 1 of "General Experimental Materials" was inoculated into a BD Difco Lactobacilli MRS (De Man, Rogosa and Sharpe) broth (Catalogue no.: DF0881-17-5), and was then cultivated in an incubator (37° C.) for 16 hours to obtain a liquid culture of *Bacillus coagulans* CB85. Next, the number of the *Bacillus coagulans* CB85 in the liquid culture was counted using a plate counting medium. After centrifugation at 10,000 rpm and 25° C. for 15 minutes, the resultant cell pellet was collected, and was then subjected to a spray-drying treatment, thereby obtaining a bacteria powder of the live *Bacillus coagulans* CB85 (abbreviated as live *Bacillus coagulans* CB85 powder) having a bacterial concentration of $1\times10^9$ CFU/g.

3. Preparation of Bacteria Powder of Heat-Killed *Lactobacillus plantarum* CB102

The *Lactobacillus plantarum* CB102 as described in section 1 of "General Experimental Materials" was inoculated into a BD Difco Lactobacilli MRS (De Man, Rogosa and Sharpe) broth (Catalogue no.: DF0881-17-5), and was then cultivated in an incubator (37° C.) for 16 hours to obtain a liquid culture of *Lactobacillus plantarum* CB102. Next, the number of the *Lactobacillus plantarum* CB102 in the liquid culture was counted using a plate counting medium. The liquid culture of *Lactobacillus plantarum* CB102 was subsequently subjected to a heat treatment using high-temperature short-time (HTST) pasteurization at 73±2° C. for 15 minutes, so as to kill the *Lactobacillus plantarum* CB102 in the liquid culture. After centrifugation at 10,000 rpm and 25° C. for 15 minutes, the resultant cell pellet was collected, and was then subjected to a spray-drying treatment, thereby obtaining a bacteria powder of the heat-killed *Lactobacillus plantarum* CB102 (abbreviated as heat-killed *Lactobacillus plantarum* CB102 powder) having a bacterial concentration of $5\times10^9$ CFU/g.

4. Preparation of Bacteria Powder Mixture of Live *Bacillus coagulans* CB85 and Heat-Killed *Lactobacillus plantarum* CB102

The live *Bacillus coagulans* CB85 powder and the heat-killed *Lactobacillus plantarum* CB102 powder prepared in section 2 and section 3 of "General Experimental Materials" were mixed in a number ratio of 1:1.47, so as to obtain a bacteria powder mixture of live *Bacillus coagulans* CB85 and heat-killed *Lactobacillus plantarum* CB102 (abbreviated as two-LAB powder mixture).

5. Experimental Mice

Female BALB/c mice (8 weeks old, with a body weight of approximately 20±1 g) used in the following experiments were purchased from BioLasco Taiwan Co., Ltd. All the experimental mice were housed in an animal room with an independent air conditioning system under the following laboratory conditions: an alternating 12-hour light and 12-hour dark cycle, a temperature maintained at 221° C., and a relative humidity maintained at 55±5%. The mice were provided with water and fed ad libitum. All experimental procedures involving the experimental mice were in compliance with the legal provision of the Animal Protection Act of Taiwan, and were carried out according to the guidelines of the Animal Care Committee of the Council of Agriculture, Taiwan.

6. Severe Acute Respiratory Syndrome Coronavirus 2 (SARS-CoV-2) Solution

The SARS-CoV-2 strain used in the following experiments was obtained from SIDSCO Biomedical Co., Ltd. (Taiwan). The SARS-CoV-2 strain was dissolved in serum free Dulbecco's Modified Eagle Medium (DMEM), so as to prepare a SARS-CoV-2 solution having a virus amount of $1\times10^6$ relative luciferase units. The SARS-CoV-2 solution was stored in a freezer at −80° C. for further experiment.

General Procedures:

1. Statistical Analysis

All the experiments described below were performed in triplicates. The experimental data of all the test groups are expressed as mean±standard error of the mean (SEM), and were analyzed using independent sample t-test, so as to evaluate the differences between the groups. Statistical significance is indicated by $p<0.05$.

Example 1. Evaluation of the Effect of Two-LAB Powder Mixture According to this Disclosure on Alleviation of Lung Inflammation, Lung Injury and Immune Abnormalities Induced by SARS-CoV-2

Experimental Procedures:

A. Administration of LAB Powder or Two-LAB Powder Mixture and Inoculation of SARS-CoV-2

First, the BALB/c mice as described in section 5 of "General Experimental Materials" were randomly divided into 6 groups (n=8 mice in each group), including a blank control group, a normal control group, a pathological control group, an experimental group, and two comparative groups (i.e., comparative groups 1 and 2). Next, the live *Bacillus coagulans* CB85 powder and the heat-killed *Lactobacillus plantarum* CB102 powder prepared in section 2 and section 3 of "General Experimental Materials", respectively, and the two-LAB powder mixture prepared in section 4 of "General Experimental Materials" were formulated in reverse osmosis water, so as to prepare a live *Bacillus coagulans* CB85 solution, a heat-killed *Lactobacillus plantarum* CB102 solution, and a two-LAB powder mixture solution, each having a bacterial concentration as shown in Table 2 below.

Afterward, the mice in each of the normal control group, the experimental group, and the comparative groups 1 and 2 were fed, via oral gavage, with the appropriate amount of the live *Bacillus coagulans* CB85 solution, the heat-killed *Lactobacillus plantarum* CB102 solution or the two-LAB powder mixture solution, so that each mouse in the normal control group, the experimental group, and the comparative groups 1 and 2 received a bacterial concentration per day as shown in Table 3. Each mouse was fed once daily for a total period of 18 days. In addition, each mouse in the blank control group and the pathological control group received no treatment.

TABLE 2

| Solution | Live *Bacillus coagulans* CB85 | Heat-killed *Lactobacillus plantarum* CB102 |
|---|---|---|
| | Bacterial concentration (CFU/mL) | |
| Live *Bacillus coagulans* CB85 solution | $6.8\times10^7$ | — |
| Heat-killed *Lactobacillus plantarum* CB102 solution | | $1.0\times10^8$ |
| Two-LAB powder mixture solution | $3.4\times10^7$ | $5.0\times10^7$ |

TABLE 3

| Group | Live *Bacillus coagulans* CB85 (CFU/day) | Heat-killed *Lactobacillus plantarum* CB102 (CFU/day) |
|---|---|---|
| Blank control group | — | — |
| Pathological control group | — | — |
| Normal control group | $3.4\times10^6$ | $5.0\times10^6$ |
| Experimental group | $3.4\times10^6$ | $5.0\times10^6$ |

TABLE 3-continued

| Group | Live *Bacillus coagulans* CB85 (CFU/day) | Heat-killed *Lactobacillus plantarum* CB102 (CFU/day) |
|---|---|---|
| Comparative group 1 | $6.8 \times 10^6$ | — |
| Comparative group 2 | — | $1.0 \times 10^7$ |

On the 15th day after the start of administration of the LAB powder or the two-LAB powder mixture, each mouse in the pathological control group, the experimental group, and the comparative groups 1 and 2 was subjected to intratracheal instillation of the SARS-CoV-2 solution prepared in section 6 of "General Experimental Materials", so that each mouse was infected with SARS-CoV-2 at a median tissue culture infectious dose ($TCID_{50}$) of $10^6$. In addition, each mouse in the blank control group and the normal control group received no treatment.

B. Determination of Lung Function

On the 15th day after the start of administration and before the inoculation of SARS-CoV-2, and on the 16th, 17th, and 18th day after the start of administration, the mice in each group were subjected to determination of respiratory parameters using Buxco FinePointe Series Whole Body Plethysmography (WBP, DSI Buxco) to assess lung function. The respiratory parameters include enhanced pause (Penh), mid-tidal expiratory flow (EF50), and ratio of time to peak expiratory flow relative to the total expiratory time (Rpef). The lower Penh and EF50 are, and the higher Rpef is, the better lung function is.

The data thus obtained were analyzed according to the procedures as described in section 1 of "General Procedures".

C. Determination of Differential Leukocyte Count in Bronchoalveolar Lavage Fluid (BALF)

On the 18th day after the start of administration, the mice in each group were sacrificed, and then the respective lung of the mice of each group was injected with 1 mL of phosphate-buffered saline (PBS) using a bronchoscope, followed by the collection of the BALF. The thus collected BALF of each mouse was subjected to centrifugation at 3,000 rpm and 4° C. for 10 minutes to form a supernatant and a pellet fraction. The supernatant was collected and was subjected to determination of concentrations of inflammatory markers described in section D of "Experimental Procedures" below. The pellet was washed and then resuspended in an appropriate amount of PBS to form a mixture. Afterwards, the mixture was subjected to determination of differential leukocyte count using a hematology analyzer (IDEXX Laboratories, Inc., Procyte Dx), so as to obtain each count of total white blood cells, lymphocyte, neutrophil, eosinophil, and basophil.

The data thus obtained were analyzed according to the procedures as described in section 1 of "General Procedures".

D. Determination of Concentrations of Inflammatory Markers in BALF

The respective supernatant prepared in section C of "Experimental Procedures" above was subjected to determination of IFN-γ, IL-4, IL-17, and IFN-β concentrations using an IFN-γ ELISA Kit (abcam, Cat. No. ab100689), an IL-4 ELISA Kit (abcam, Cat. No. abl00710), an IL-17 ELISA Kit (abcam, Cat. No. ab100702), and IFN-β ELISA Kit (Elabscience, Cat. No. E-EL-M0033), respectively, in accordance with the manufacturer's instructions. The thus obtained absorbance values of IFN-γ, IL-4, IL-17, and IFN-β of the mice in each group were converted to their concentrations expressed in pg/mL according to standard curves prepared in advance using standards with different known concentrations of IFN-γ, IL-4, IL-17, and IFN-β, respectively.

The data thus obtained were analyzed according to the procedures as described in section 1 of "General Procedures".

E. Histopathologic Analysis of Lung Tissue

After completing the experiments in section C and section D of "Experimental Procedures" above, the lung tissue was obtained from the respective mouse carcass. The lung tissue was subjected to a fixation treatment with a 10% formalin at room temperature for 10 hours. The fixed tissue sample was then embedded in paraffin, followed by slicing to obtain a tissue section with a thickness ranging from 2 μm to 5 μm.

The tissue section was subjected to hematoxylin-eosin staining using a staining protocol well-known to those skilled in the art, and was then observed under an optical microscope (Manufacturer: Leica; Model no.: LED 2500) at a magnification of 100× to 400×. One area of the respective tissue section was randomly selected and photographed, and the severity of lung injury, including edema, alveolar and interstitial inflammation, alveolar and interstitial hemorrhage, atelectasis, and hyaline membrane formation, in the respective tissue section was assessed by a veterinary pathologist of National Chung-Hsing University, Taichung, Taiwan, according to the methods described in H K Bayes, et al. (2016) Sci. Rep. doi: 10.1038/srep35838. The severity of lung injury was graded by pathological score on a scale of 1 to 4. The higher the scale is, the greater the area of lung injury is.

The data thus obtained were analyzed according to the procedures as described in section 1 of "General Procedures".

Results:

A. Determination of Lung Function

Figure 2:
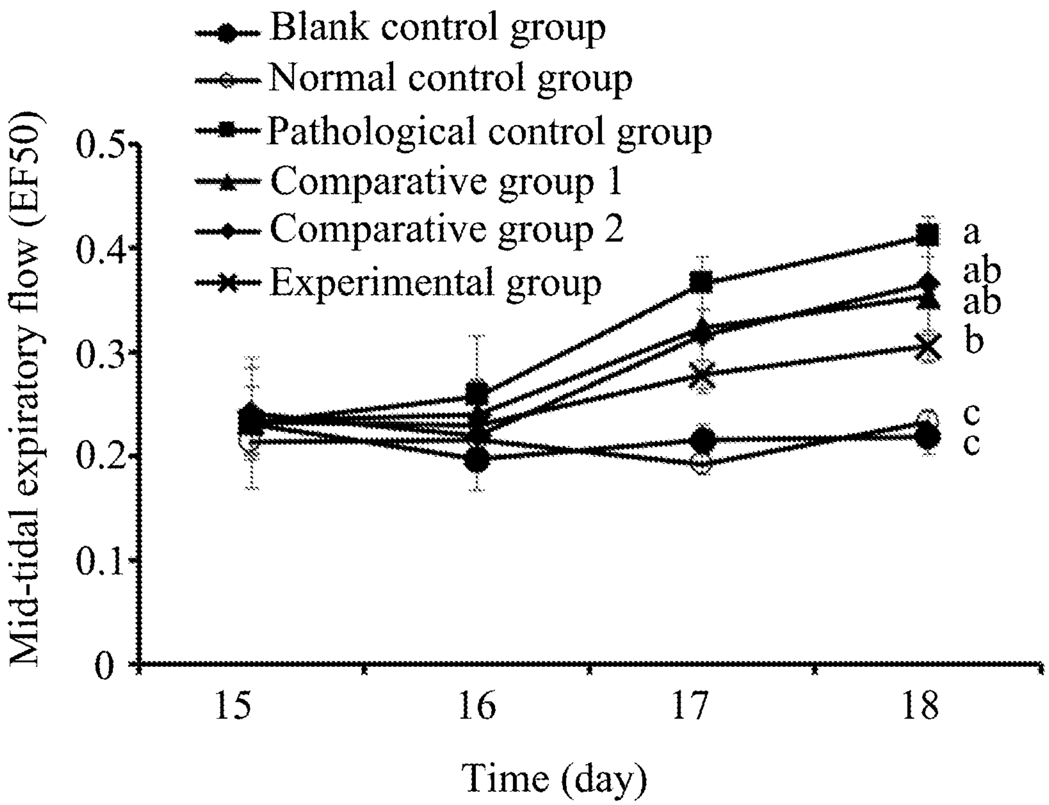
FIG. 2 shows the change in mid-tidal expiratory flow (EF50) determined over time in each group of mice of Example 1, infra, in which: the English letters indicate the results of statistical analyses; if any two groups have the same English letter, there is no significant difference between the two groups; and if any two groups do not have the same English letter, there is a significant difference between the two groups ($p<0.05$).
Figure 3:
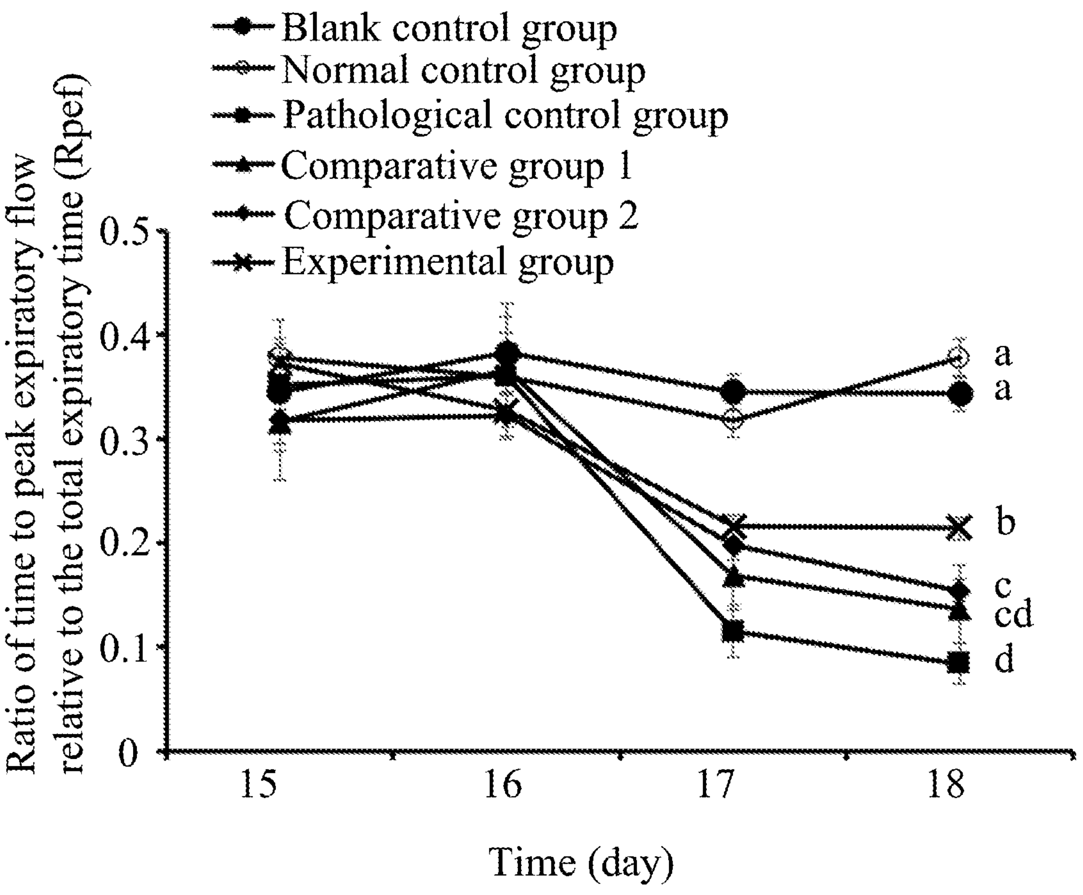
FIG. 3 shows the change in ratio of time to peak expiratory flow relative to the total expiratory time (Rpef) determined over time in each group of mice of Example 1, infra, in which: the English letters indicate the results of statistical analyses; if any two groups have the same English letter, there is no significant difference between the two groups; and if any two groups do not have the same English letter, there is a significant difference between the two groups ($p<0.05$).
Figure 4:
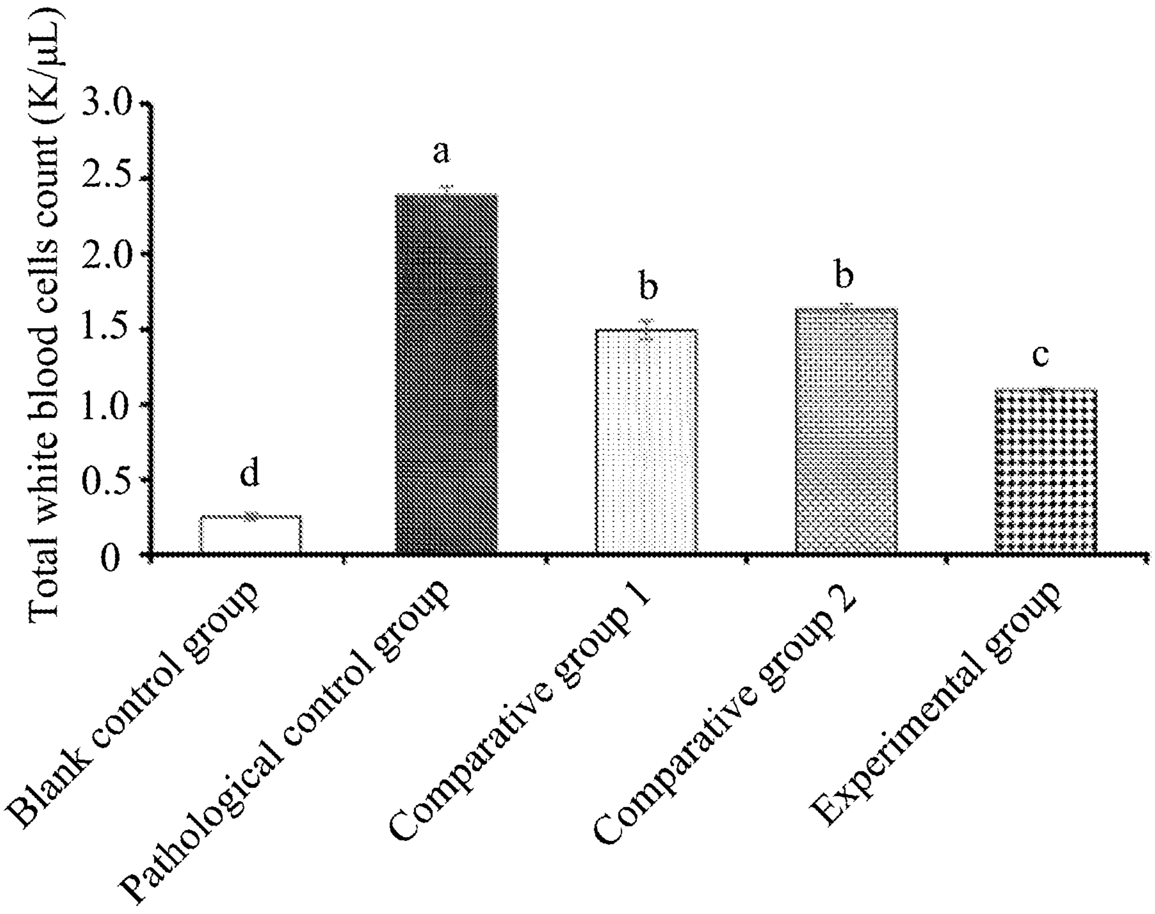
FIG. 4 shows the total white blood cells count determined in the bronchoalveolar lavage fluid (BALF) of each group of mice in Example 1, infra, in which: the English letters indicate the results of statistical analyses; if any two groups have the same English letter, there is no significant difference between the two groups; and if any two groups do not have the same English letter, there is a significant difference between the two groups ($p<0.05$).
Figure 5:
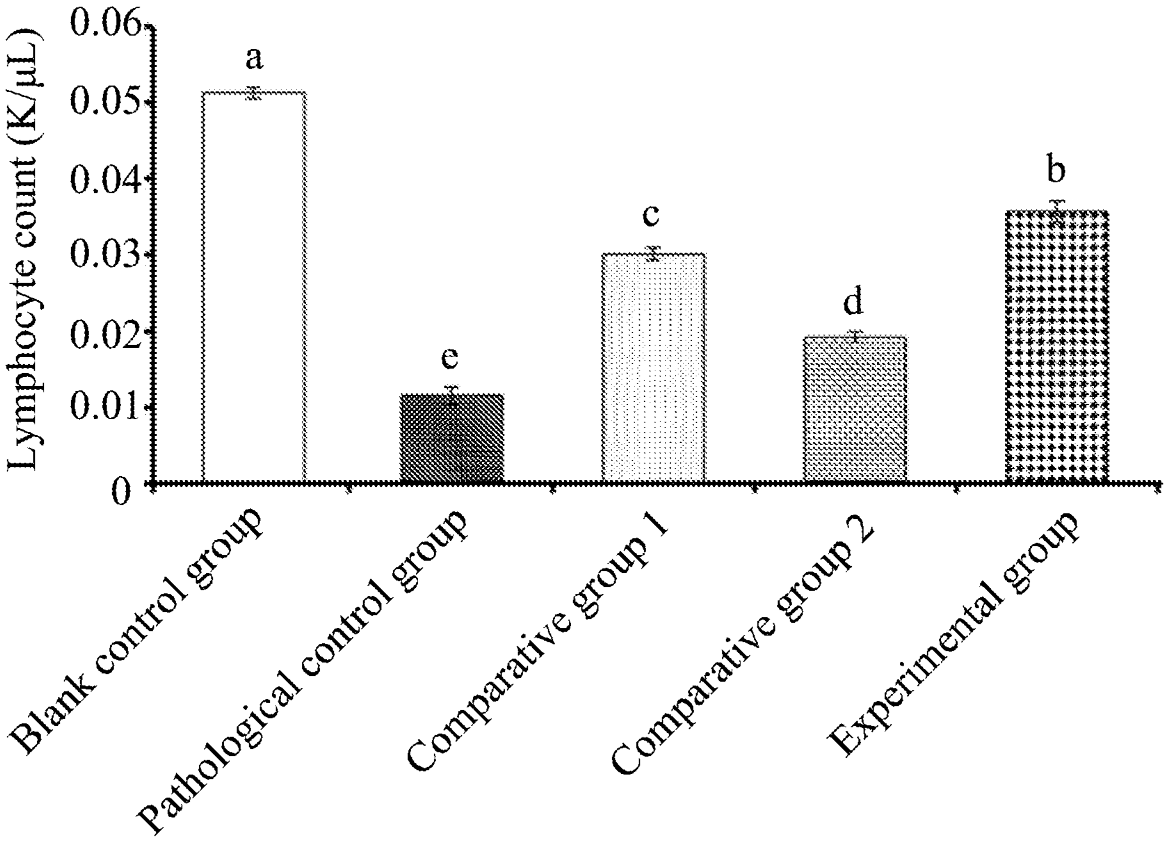
FIG. 5 shows the lymphocyte count determined in the BALF of each group of mice in Example 1, infra, in which: the English letters indicate the results of statistical analyses; if any two groups have the same English letter, there is no significant difference between the two groups; and if any two groups do not have the same English letter, there is a significant difference between the two groups ($p<0.05$).
Figure 6:
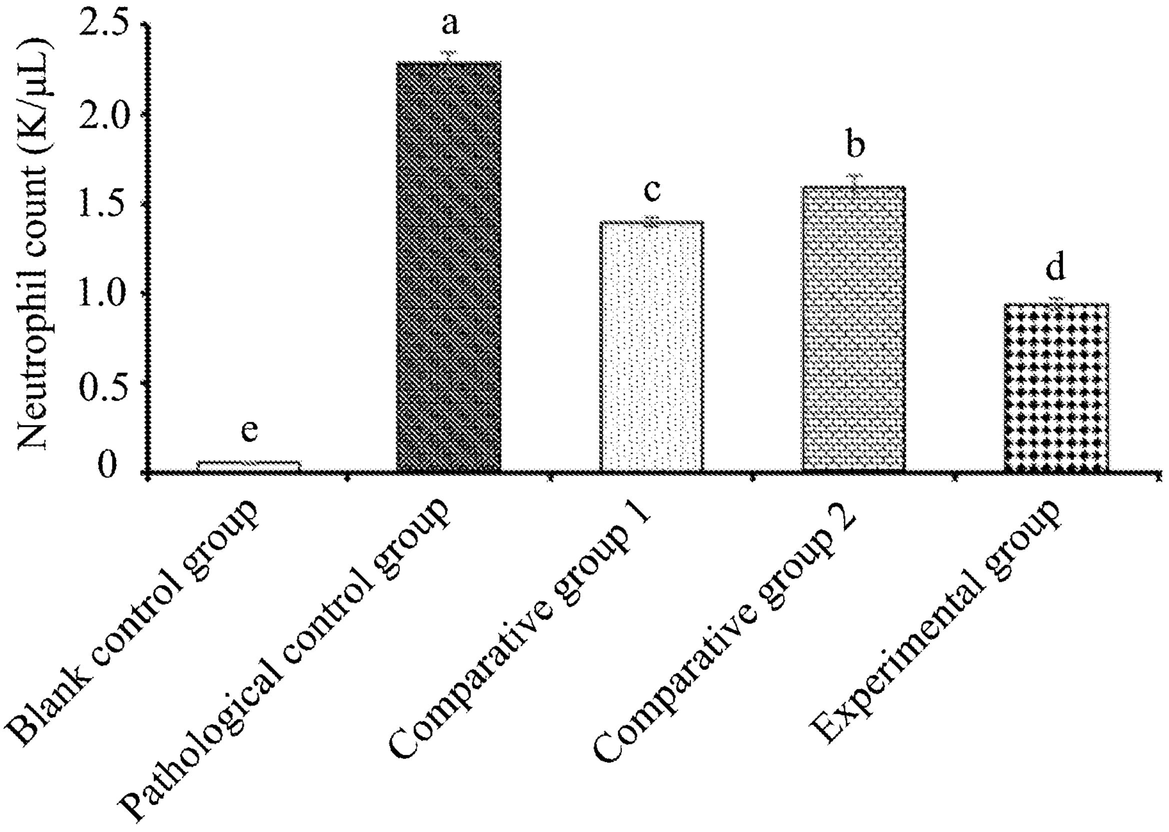
FIG. 6 shows the neutrophil count determined in the BALF of each group of mice in Example 1, infra, in which: the English letters indicate the results of statistical analyses; if any two groups have the same English letter, there is no significant difference between the two groups; and if any two groups do not have the same English letter, there is a significant difference between the two groups ($p<0.05$).
Figure 7:
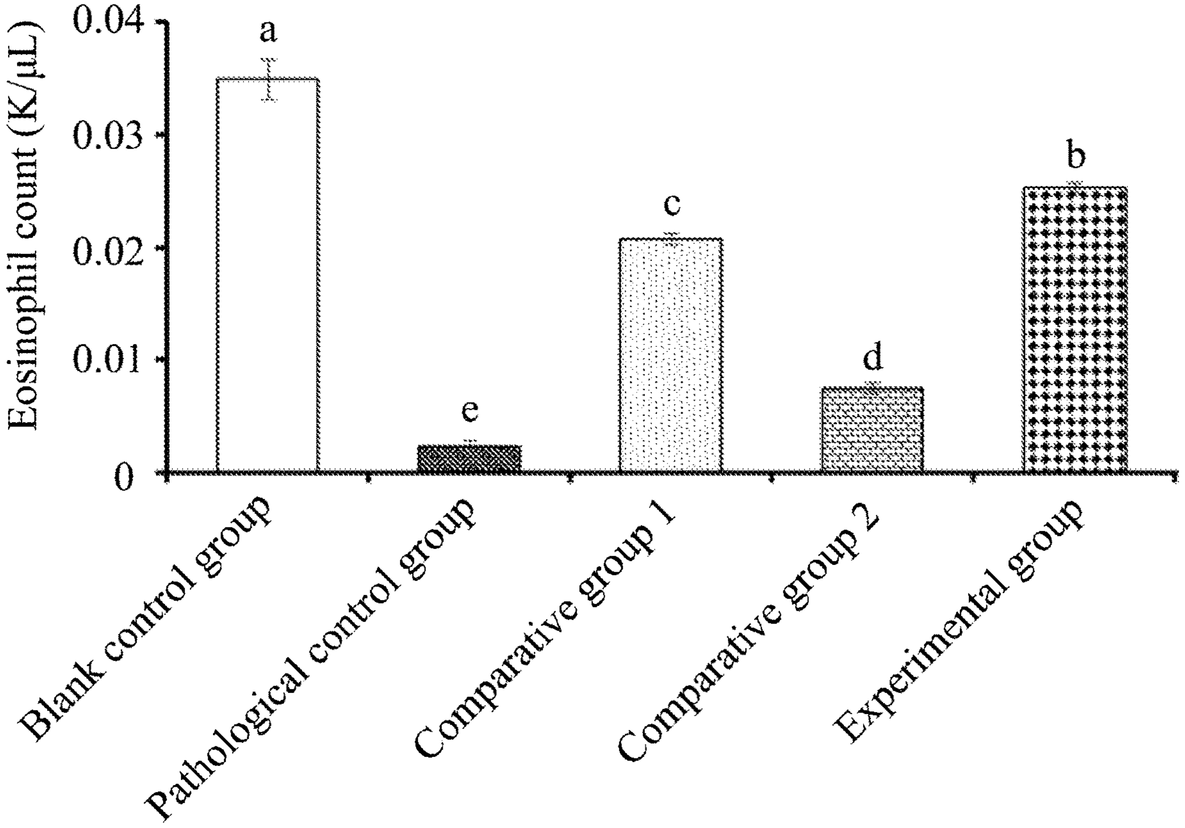
FIG. 7 shows the eosinophil count determined in the BALF of each group of mice in Example 1, infra, in which: the English letters indicate the results of statistical analyses; if any two groups have the same English letter, there is no significant difference between the two groups; and if any two groups do not have the same English letter, there is a significant difference between the two groups ($p<0.05$).
Figure 8:
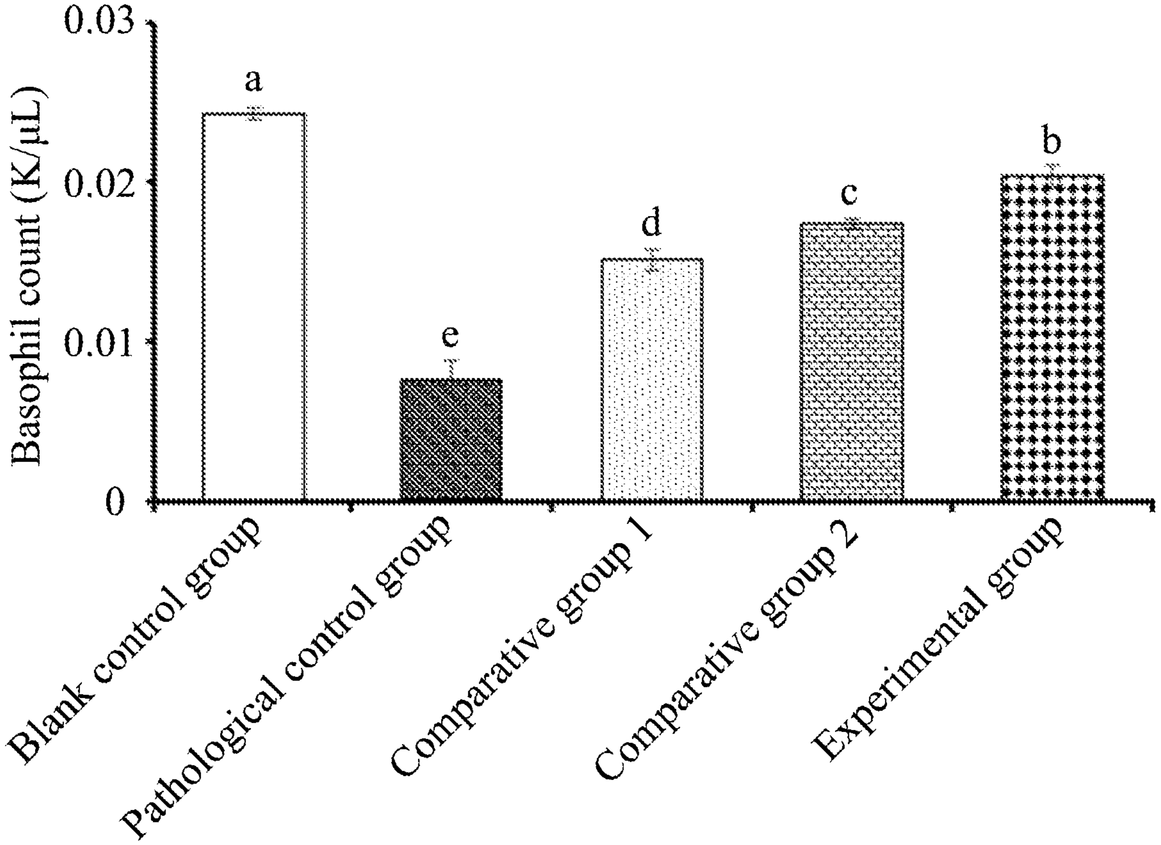
FIG. 8 shows the basophil count determined in the BALF of each group of mice in Example 1, infra, in which: the English letters indicate the results of statistical analyses; if any two groups have the same English letter, there is no significant difference between the two groups; and if any two groups do not have the same English letter, there is a significant difference between the two groups ($p<0.05$).
Figure 9:
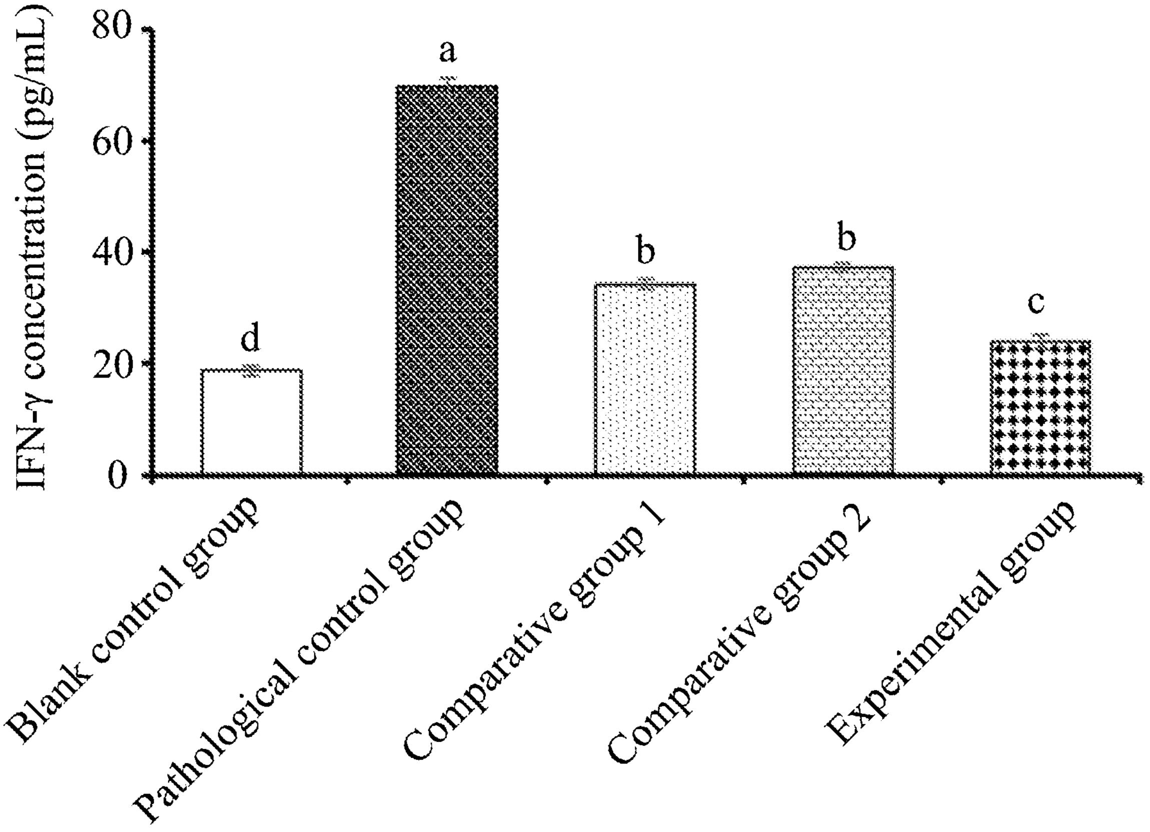
FIG. 9 shows the IFN-γ concentration determined in the BALF of each group of mice in Example 1, infra, in which: the English letters indicate the results of statistical analyses; if any two groups have the same English letter, there is no significant difference between the two groups; and if any two groups do not have the same English letter, there is a significant difference between the two groups ($p<0.05$).
Figure 10:
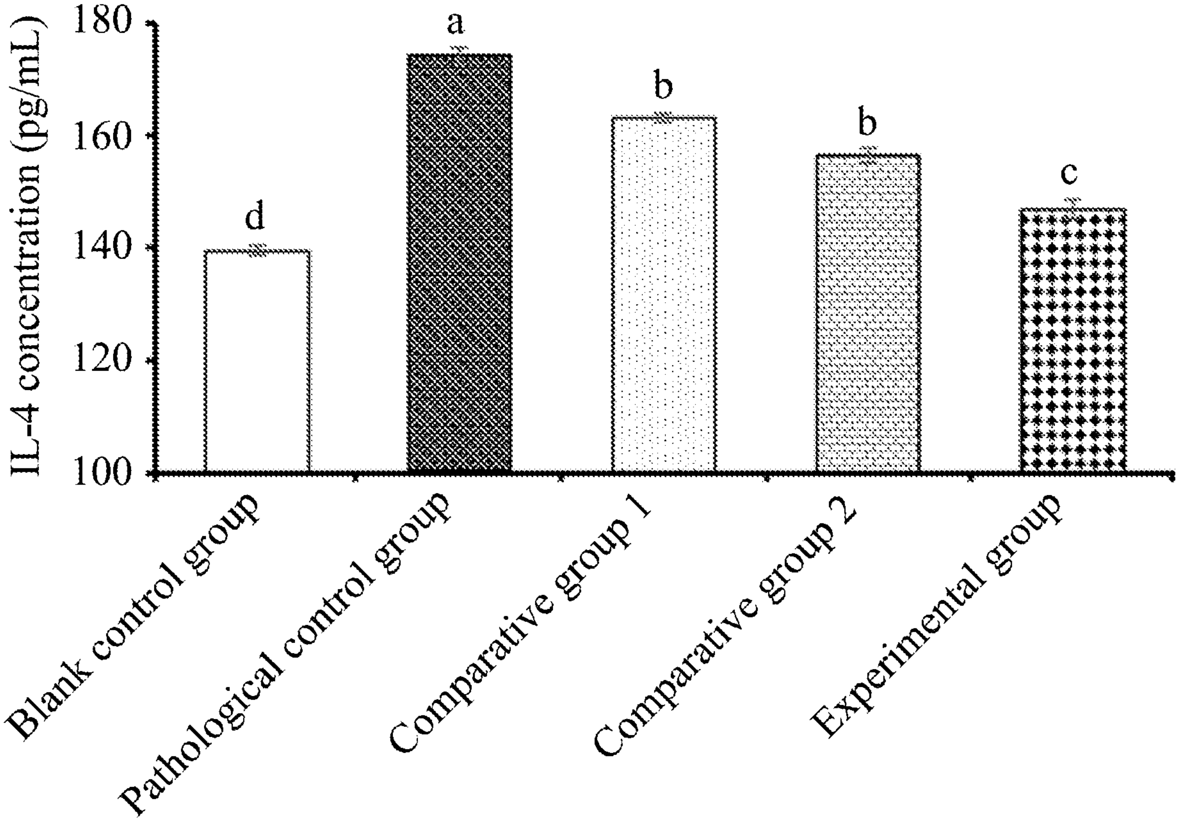
FIG. 10 shows the IL-4 concentration determined in the BALF of each group of mice in Example 1, infra, in which: the English letters indicate the results of statistical analyses; if any two groups have the same English letter, there is no significant difference between the two groups; and if any two groups do not have the same English letter, there is a significant difference between the two groups ($p<0.05$).
Figure 11:
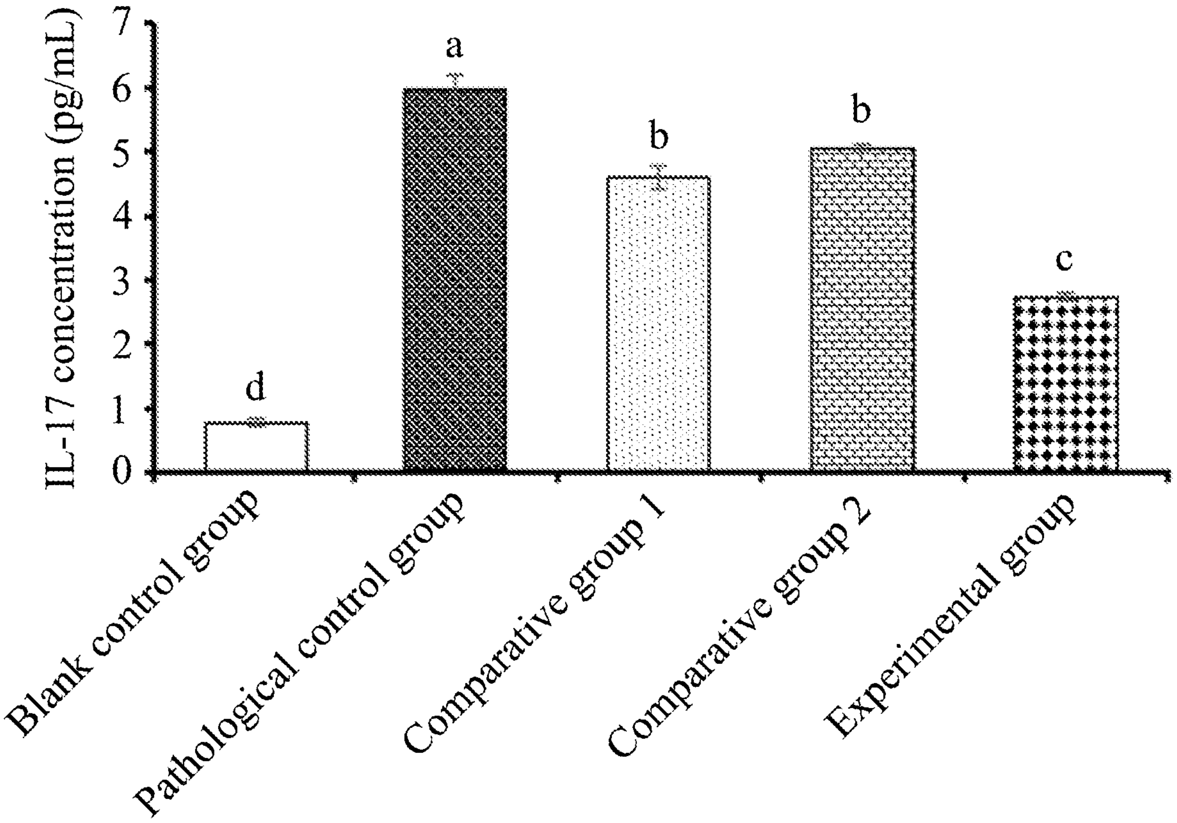
FIG. 11 shows the IL-17 concentration determined in the BALF of each group of mice in Example 1, infra, in which: the English letters indicate the results of statistical analyses; if any two groups have the same English letter, there is no significant difference between the two groups; and if any two groups do not have the same English letter, there is a significant difference between the two groups ($p<0.05$).
Figure 12:
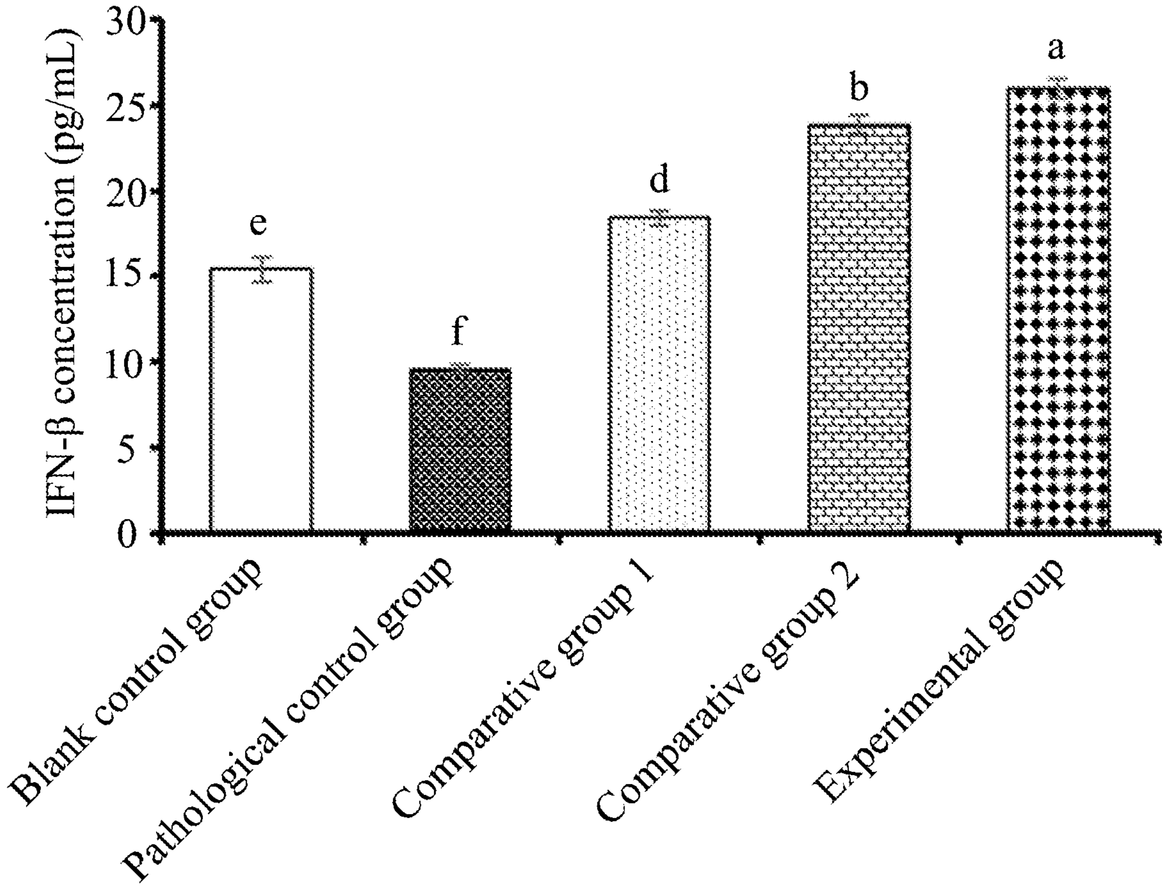
FIG. 12 shows the IFN-β concentration determined in the BALF of each group of mice in Example 1, infra, in which: the English letters indicate the results of statistical analyses; if any two groups have the same English letter, there is no significant difference between the two groups; and if any two groups do not have the same English letter, there is a significant difference between the two groups ($p<0.05$).

FIGS. 1 to 3 show the changes in enhanced pause (Penh), mid-tidal expiratory flow (EF50), and ratio of time to peak expiratory flow relative to the total expiratory time (Rpef) determined over time in each group of mice, respectively. As shown in FIGS. 1 to 3, the absence of statistical differences in the Penh, EF50 and Rpef between the blank control group and the normal control group indicates that the two-LAB powder mixture does not affect the lung function in normal mice. Compared with the blank control group, the Penh and EF50 increased rapidly over time while the Rpef decreased rapidly over time in the pathological control group, demonstrating that SARS-CoV-2 is detrimental to the lung function and causes airway obstruction. In addition, compared with the pathological control group, the increase in the Penh and EF50, and the decrease in the Rpef were significantly reduced in the experimental group, and such decreases were also superior to those in the comparative groups 1 and 2. In particular, the EF50 and Rpef determined in the comparative group 1 had no statistical difference compared with those of the pathological control group, and the EF50 determined in the comparative group 2 also had no statistical difference compared with that of the pathological control group. These results indicate that the live *Bacillus coagulans* CB85 powder and the heat-killed *Lactobacillus plantarum* CB102 powder, when mixed in a specific number ratio of 1:1.47 to prepare a two-LAB powder mixture, can effectively improve lung function of the mice, and such effect is significantly better than the use of the live *Bacillus coagulans* CB85 powder or the heat-killed *Lactobacillus plantarum* CB102 powder alone.

B. Determination of Differential Leukocyte Count in BALF

FIGS. 4 to 8 show the counts of total white blood cells, lymphocyte, neutrophil, eosinophil, and basophil determined in the BALF of each group of mice. As shown in FIGS. 4 to 8, compared with the blank control group, the respective count of total white blood cells and neutrophil determined in the pathological control group showed a significant increase while the respective count of lymphocyte, eosinophil, and basophil determined in the pathological control group showed a significant decrease, indicating that SARS-CoV-2 can lead to lymphopenia and granulocyte abnormalities in the mice. In addition, compared with the pathological control group, the respective count of total white blood cells and neutrophil determined in the experimental group and the comparative groups 1 and 2 showed a significant decrease, whereas the respective count of lymphocyte, eosinophil, and basophil determined in the experimental group and the comparative groups 1 and 2 showed a significant increase. In particular, the respective count of total white blood cells and neutrophil determined in the experimental group was significantly lower than those of the comparative groups 1 and 2, and the respective count of lymphocyte, eosinophil, and basophil determined in the experimental group was significantly higher than those of the comparative groups 1 and 2. These results demonstrate that the live *Bacillus coagulans* CB85 powder and the heat-killed *Lactobacillus plantarum* CB102 powder, when mixed in a specific number ratio of 1:1.47 to prepare a two-LAB powder mixture, can effectively alleviate lymphopenia and granulocyte abnormalities in the mice, and such effect is significantly better than the use of the live *Bacillus coagulans* CB85 powder or the heat-killed *Lactobacillus plantarum* CB102 powder alone.

C. Determination of Concentrations of Inflammatory Markers in BALF

FIGS. 9 to 12 show the concentrations of IFN-γ, IL-4, IL-17, and IFN-β determined in the BALF of each group of mice. As shown in FIGS. 9 to 12, compared with the blank control group, the respective concentration of IFN-γ, IL-4, and IL-17 determined in the pathological control group showed a significant increase while the concentration of IFN-β determined in the pathological control group showed a significant decrease, demonstrating that SARS-CoV-2 can induce lung inflammation in the mice. In addition, compared with the pathological control group, the respective concentration of IFN-γ, IL-4, and IL-17 determined in the experimental group and the comparative groups 1 and 2 showed a significant decrease, whereas the concentration of IFN-β determined in each of the experimental group and the comparative groups 1 and 2 showed a significant increase. In particular, the respective concentration of IFN-γ, IL-4, and IL-17 determined in the experimental group was significantly lower than those of the comparative groups 1 to 2, and the concentration of IFN-β determined in the experimental group was significantly higher than that of the comparative groups 1 and 2. These results indicate that the live *Bacillus coagulans* CB85 powder and the heat-killed *Lactobacillus plantarum* CB102 powder, when mixed in a specific number ratio of 1:1.47 to prepare a two-LAB powder mixture, can effectively alleviate lung inflammation in the mice, and such effect is significantly better than the use of the live *Bacillus coagulans* CB85 powder or the heat-killed *Lactobacillus plantarum* CB102 powder alone.

D. Histopathologic Analysis of Lung Tissue

Figure 13:
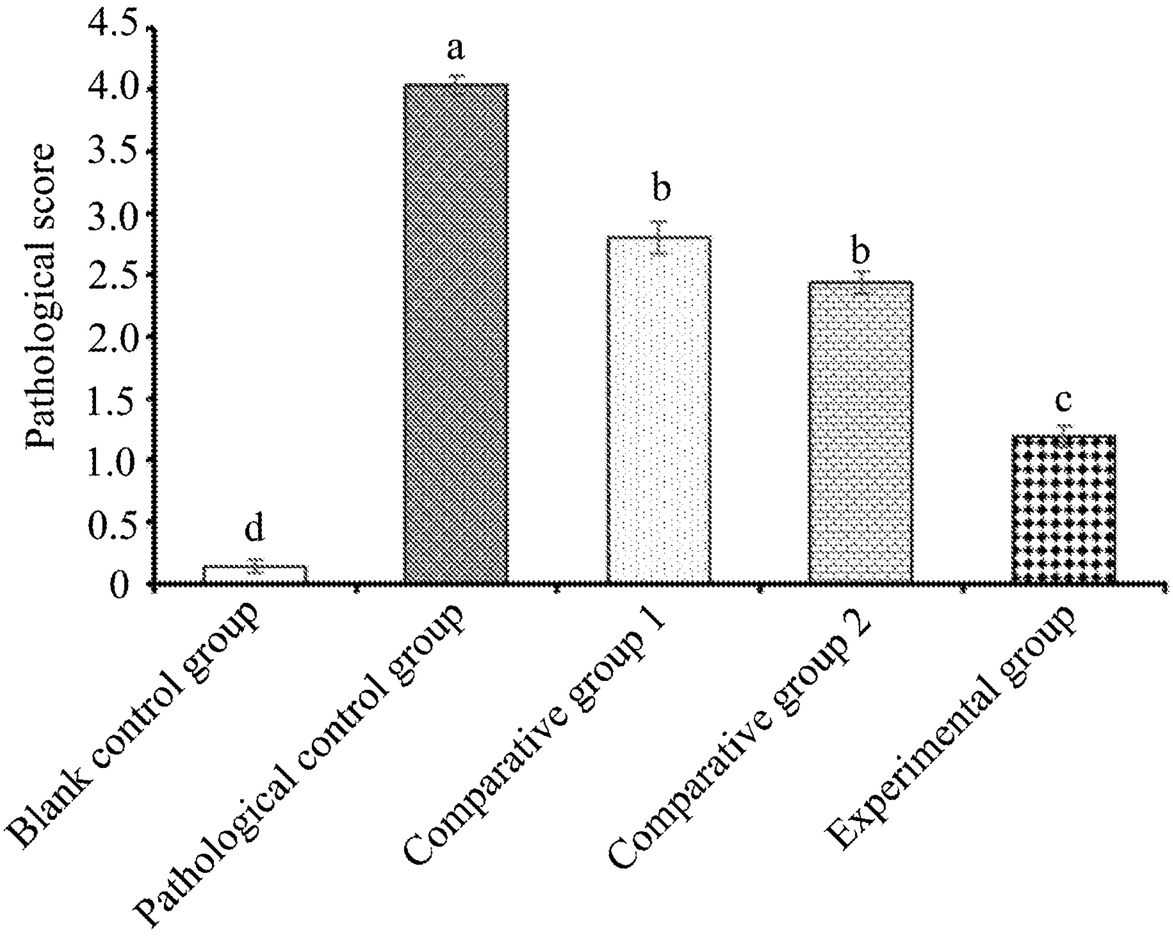
FIG. 13 shows the pathological score of the lung tissue analyzed by hematoxylin-eosin staining in each group of mice in Example 1, infra, in which: the English letters indicate the results of statistical analyses; if any two groups have the same English letter, there is no significant difference between the two groups; and if any two groups do not have the same English letter, there is a significant difference between the two groups ($p<0.05$).

FIG. 13 shows the pathological score of the lung tissue analyzed by hematoxylin-eosin staining in each group of mice. As shown in FIG. 13, compared with the blank control group, the pathological score determined in the pathological control group showed a significant increase, indicating that SARS-CoV-2 can induce lung injury in the mice. In addition, compared with the pathological control group, the respective pathological score determined in the experimental group and the comparative groups 1 and 2 showed a significant decrease. In particular, the pathological score determined in the experimental group was significantly lower than those of the comparative groups 1 and 2. These results demonstrate that the live *Bacillus coagulans* CB85 powder and the heat-killed *Lactobacillus plantarum* CB102 powder, when mixed in a specific number ratio of 1:1.47 to prepare a two-LAB powder mixture, can effectively alleviate lung injury in the mice, and such effect is significantly better than the use of the live *Bacillus coagulans* CB85 powder or the heat-killed *Lactobacillus plantarum* CB102 powder alone.

Summarizing the above test results, it is clear that compared with the use of the live *Bacillus coagulans* CB85 powder or the heat-killed *Lactobacillus plantarum* CB102 powder alone, the live *Bacillus coagulans* CB85 powder and the heat-killed *Lactobacillus plantarum* CB102 powder, when mixed in a specific number ratio of 1:1.47 to prepare a two-LAB powder mixture, can significantly improve lung function, and alleviate lung inflammation, lung injury and immune abnormalities induced by SARS-CoV-2, and hence can effectively prevent SARS-CoV-2 infection-associated disorder.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for preventing a severe acute respiratory syndrome coronavirus 2 (SARS-COV-2) infection-associated disorder, comprising administering to a subject in need thereof a composition including live *Bacillus coagulans* CB85 which is deposited under the Budapest Treaty at the Deutsche Sammlung von Mikroorganismen und Zellkulturen (DSMZ) GmbH under an accession number DSM 33893, and heat-killed *Lactobacillus plantarum* CB102 which is deposited under the Budapest Treaty at the DSMZ GmbH under an accession number DSM 33894, wherein the SARS-COV-2 infection-associated disorder is selected from the group consisting of lung inflammation, lung injury, lymphopenia, granulocyte abnormalities, and combinations thereof.

2. The method as claimed in claim 1, wherein a number ratio of *Bacillus coagulans* CB85 and *Lactobacillus plantarum* CB102 ranges from 1:0.1 to 1:10.

3. The method as claimed in claim 1, wherein the composition is a food product or a pharmaceutical composition.

4. The method as claimed in claim 3, wherein the pharmaceutical composition is in a dosage form for oral administration.

* * * * *